United States Patent
Barker

(10) Patent No.: US 8,469,971 B2
(45) Date of Patent: Jun. 25, 2013

(54) STYLET FOR GUIDING LEADS OF IMPLANTABLE ELECTRIC STIMULATION SYSTEMS AND METHODS OF MAKING AND USING

(75) Inventor: John Michael Barker, Ventura, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 894 days.

(21) Appl. No.: 12/535,452

(22) Filed: Aug. 4, 2009

(65) Prior Publication Data

US 2010/0042109 A1    Feb. 18, 2010

Related U.S. Application Data

(60) Provisional application No. 61/088,292, filed on Aug. 12, 2008.

(51) Int. Cl.
*A61B 19/00* (2006.01)

(52) U.S. Cl.
USPC .......................................... 606/129

(58) Field of Classification Search
USPC ........... 606/129; 485/816; 439/816; 607/116, 607/122; 600/585; 24/136 R
See application file for complete search history.

(56) References Cited

U.S. PATENT DOCUMENTS

| | | | |
|---|---|---|---|
| 3,974,834 A | 8/1976 | Kane | |
| 4,209,019 A | 6/1980 | Dutcher et al. | |
| 4,467,817 A | 8/1984 | Harris | |
| 4,585,013 A | 4/1986 | Harris | |
| 4,656,698 A * | 4/1987 | Arakawa | 24/136 A |
| 4,721,118 A | 1/1988 | Harris | |
| 4,791,939 A | 12/1988 | Maillard | |
| 4,924,881 A | 5/1990 | Brewer | |
| 5,325,868 A * | 7/1994 | Kimmelstiel | 600/585 |
| 5,728,148 A * | 3/1998 | Bostrom et al. | 607/116 |
| 6,104,960 A | 8/2000 | Duysens et al. | |

(Continued)

FOREIGN PATENT DOCUMENTS

| | | |
|---|---|---|
| EP | 0013605 A1 | 7/1980 |
| EP | 1574232 A1 | 9/2005 |

(Continued)

OTHER PUBLICATIONS

U.S. Appl. No. 11/238,240, filed Sep. 29, 2005 (20 pgs.).

*Primary Examiner* — Gary Jackson
*Assistant Examiner* — Martin Ton
(74) *Attorney, Agent, or Firm* — Frommer Lawrence & Haug LLP; Patrick R. Turner

(57) ABSTRACT

A lead assembly includes a lead and a stylet. The lead has a distal end, a proximal end, and an outer lead covering. The lead includes a plurality of electrodes disposed at the distal end, a plurality of terminals disposed at the proximal end, and at least one lumen defined in the lead that extends from the distal end to the proximal end. The lead also includes a plurality of conductive wires electrically coupling the plurality of electrodes to the plurality of terminals. The stylet is configured and arranged for inserting into one of the at least one lumens of the lead. The stylet includes an elongated body and a protective feature that is coupled to the elongated body. The protective feature is configured and arranged for absorbing or redirecting an amount of force applied to the stylet above a threshold amount of force.

12 Claims, 8 Drawing Sheets

U.S. PATENT DOCUMENTS

| | | |
|---|---|---|
| 6,181,969 B1 | 1/2001 | Gord |
| 6,389,320 B1 | 5/2002 | Pianca |
| 6,516,227 B1 | 2/2003 | Meadows et al. |
| 6,607,496 B1 | 8/2003 | Poor et al. |
| 6,609,029 B1 | 8/2003 | Mann et al. |
| 6,609,032 B1 | 8/2003 | Woods et al. |
| 6,611,710 B2 | 8/2003 | Gomperz et al. |
| 6,741,892 B1 * | 5/2004 | Meadows et al. ............ 607/116 |
| 6,747,892 B2 * | 6/2004 | Khalid .................... 365/185.03 |
| 6,944,506 B1 * | 9/2005 | Morgan et al. ................ 607/122 |
| 6,970,747 B2 * | 11/2005 | Kokones et al. ............. 607/116 |
| 6,978,180 B2 | 12/2005 | Tadlock |
| 7,033,326 B1 | 4/2006 | Pianca et al. |
| 7,072,703 B2 * | 7/2006 | Zhang et al. .................. 600/374 |
| 7,177,701 B1 | 2/2007 | Pianca |
| 7,181,290 B2 | 2/2007 | Chitre et al. |
| 7,244,150 B1 | 7/2007 | Brase et al. |
| 7,343,205 B1 | 3/2008 | Pianca et al. |
| 7,349,743 B2 | 3/2008 | Tadlock |
| 7,379,776 B1 | 5/2008 | Chitre et al. |
| 7,450,997 B1 | 11/2008 | Pianca et al. |
| 7,486,995 B2 | 2/2009 | Tadlock |
| 7,519,432 B2 | 4/2009 | Bolea et al. |
| 7,972,282 B2 * | 7/2011 | Clark et al. .................. 600/585 |
| 2002/0065543 A1 | 5/2002 | Gomperz et al. |
| 2003/0114905 A1 | 6/2003 | Kuzma |
| 2003/0135253 A1 | 7/2003 | Kokones et al. |
| 2004/0059392 A1 | 3/2004 | Parramon et al. |
| 2004/0186532 A1 | 9/2004 | Tadlock |
| 2004/0243206 A1 | 12/2004 | Tadlock |
| 2004/0249429 A1 | 12/2004 | Tadlock |
| 2005/0107861 A1 | 5/2005 | Harris et al. |
| 2005/0165465 A1 | 7/2005 | Pianca et al. |
| 2005/0203603 A1 | 9/2005 | Chitre et al. |
| 2006/0089691 A1 | 4/2006 | Kaplan et al. |
| 2006/0089692 A1 | 4/2006 | Cross et al. |
| 2006/0089695 A1 | 4/2006 | Bolea et al. |
| 2006/0089696 A1 | 4/2006 | Olsen et al. |
| 2006/0089697 A1 | 4/2006 | Cross et al. |
| 2006/0136008 A1 | 6/2006 | Tadlock |
| 2006/0258193 A1 | 11/2006 | Hoecke et al. |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0219467 A1 * | 9/2007 | Clark et al. .................. 600/585 |
| 2007/0219595 A1 | 9/2007 | He |
| 2007/0233214 A1 | 10/2007 | Chitre et al. |
| 2007/0239243 A1 | 10/2007 | Moffitt et al. |
| 2008/0071320 A1 | 3/2008 | Brase |
| 2008/0114433 A1 | 5/2008 | Sage et al. |
| 2009/0187222 A1 | 7/2009 | Barker |

FOREIGN PATENT DOCUMENTS

| | | |
|---|---|---|
| WO | 03059440 A2 | 7/2003 |
| WO | 2004062470 A2 | 7/2004 |
| WO | 2005032650 A1 | 4/2005 |
| WO | 2006047145 A1 | 5/2006 |
| WO | 2006047168 A1 | 5/2006 |
| WO | 2006047177 A1 | 5/2006 |
| WO | 2006047178 A1 | 5/2006 |
| WO | 2006047179 A1 | 5/2006 |
| WO | 2009094364 A1 | 7/2009 |

* cited by examiner

STYLET FOR GUIDING LEADS OF IMPLANTABLE ELECTRIC STIMULATION SYSTEMS AND METHODS OF MAKING AND USING

CROSS-REFERENCE TO RELATED APPLICATIONS

This application is a utility patent application based on a previously filed U.S. Provisional Patent Application Ser. No. 61/088,292 filed on Aug. 12, 2008, the benefit of which is hereby claimed under 35 U.S.C. §119(e) and incorporated herein by reference.

TECHNICAL FIELD

The present invention is directed to the area of implantable electrical stimulation systems and methods of making and using the systems. The present invention is also directed to implantable electrical stimulation systems including stylets for facilitating the guiding of leads, the stylets configured and arranged for preventing or reducing the possibility of damaging or puncturing a lead, as well as methods of making and using the stylets, leads, and implantable electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes disposed on each lead. The stimulator electrodes are in contact with or near the nerves, muscles, or other tissue to be stimulated. The pulse generator in the control module generates electrical pulses that are delivered by the electrodes to body tissue. Stylets are typically employed during implantation of the stimulator to facilitate placement of one or more arrays of stimulator electrodes at or near the tissue to be stimulated.

BRIEF SUMMARY

In one embodiment, a lead assembly includes a lead and a stylet. The lead has a distal end, a proximal end, and an outer lead covering. The lead includes a plurality of electrodes disposed at the distal end, a plurality of terminals disposed at the proximal end, and at least one lumen defined in the lead that extends from the distal end to the proximal end. The lead also includes a plurality of conductive wires electrically coupling the plurality of electrodes to the plurality of terminals. The stylet is configured and arranged for inserting into one of the at least one lumens of the lead. The stylet includes an elongated body, with a distal portion and a proximal portion, and a protective feature that is coupled to the elongated body. The protective feature is configured and arranged for absorbing or redirecting an amount of force applied to the stylet above a threshold amount of force.

In another embodiment, a stylet includes an elongated body and a cap. The elongated body has a distal portion, a proximal portion, and a proximal tip. The cap has a proximal end and a distal end. The cap includes an inner housing, an outer housing, and a compressed spring. The inner housing defines a central lumen. The central lumen is configured and arranged to receive the proximal portion of the elongated body. The inner housing includes an interference flange and at least one clamping member. The at least one clamping member is configured and arranged for providing resistive force against the elongated body. The outer housing includes an outer flange that is configured and arranged to press against at least one of the clamping members. The compressed spring is positioned between the interference flange and the outer flange. An initial compression value of the compressed spring at least partially determines the amount of force with which the outer flange presses against at least one of the clamping members.

In yet another embodiment, a method for stimulating patient tissue includes disposing a distal portion of a stylet into one or more lumens defined in a lead. The lead and stylet are inserted into a patient. The lead includes a plurality of electrodes disposed on a distal end that are electrically coupled to a plurality of terminals disposed on a proximal end by a plurality of conductive wires electrically coupling at least one terminal to at least one electrode. The lead and stylet are guided to a desired location in the patient using a cap disposed on a proximal portion of the stylet. The stylet includes a protective feature to absorb or redirect an amount of force applied to the cap above a preselected force threshold while guiding the lead and stylet. The stylet is removed from the lead. The proximal end of the lead is disposed into a connector. The connector defines a port for receiving the proximal end of the lead. The port includes a plurality of connective contacts that electrically couple to at least one of the plurality of terminals. The connector is electrically coupled to a control module. Electrical signals are provided from the control module to electrically stimulate patient tissue using at least one of the electrodes on the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems including stylets for facilitating the guiding of leads, the stylets configured and arranged for preventing or reducing the possibility of damaging or puncturing a lead, as well as methods of making and using the stylets, leads, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
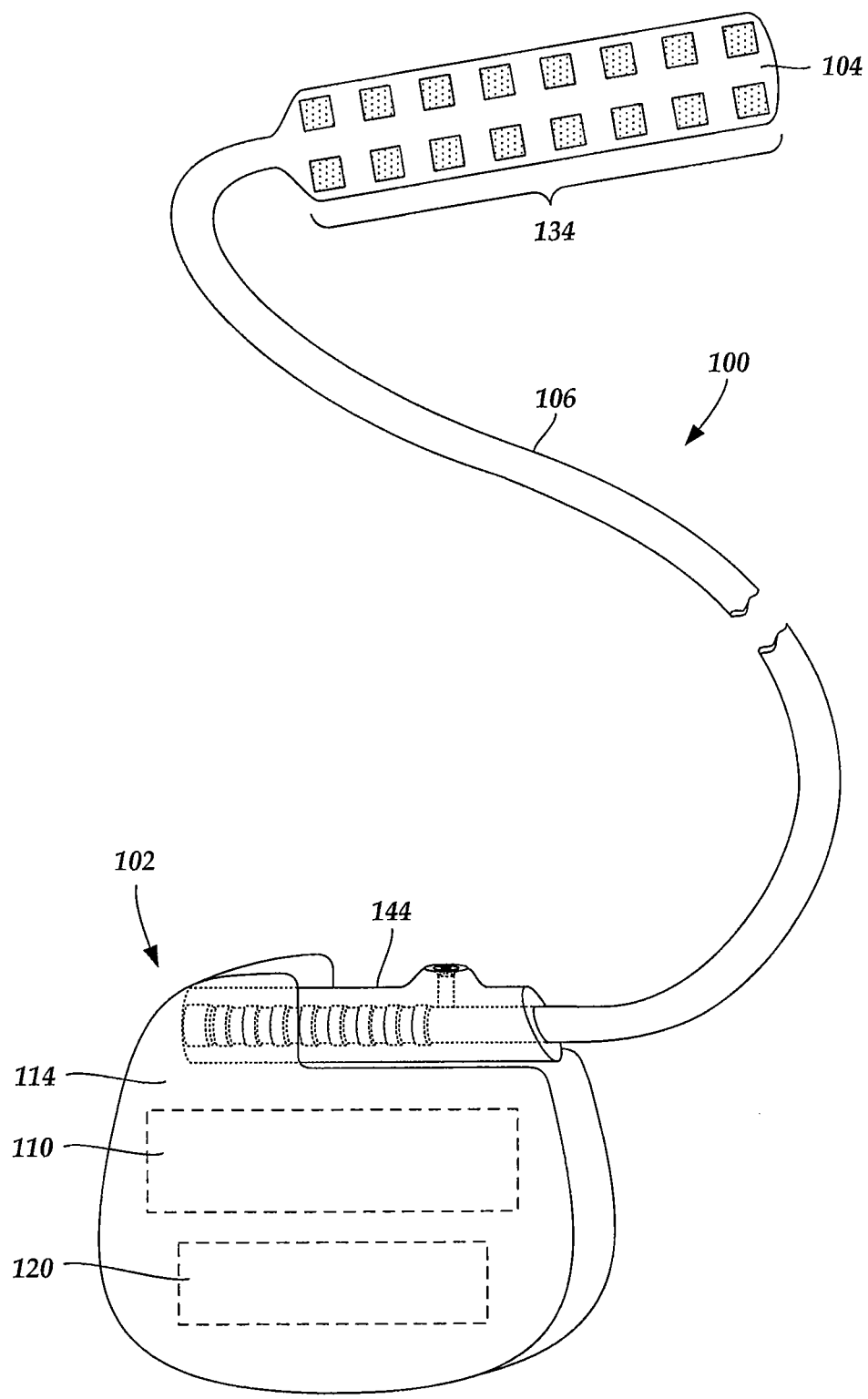
FIG. 1 is a schematic view of one embodiment of an electrical stimulation system, according to the invention.
Figure 2:
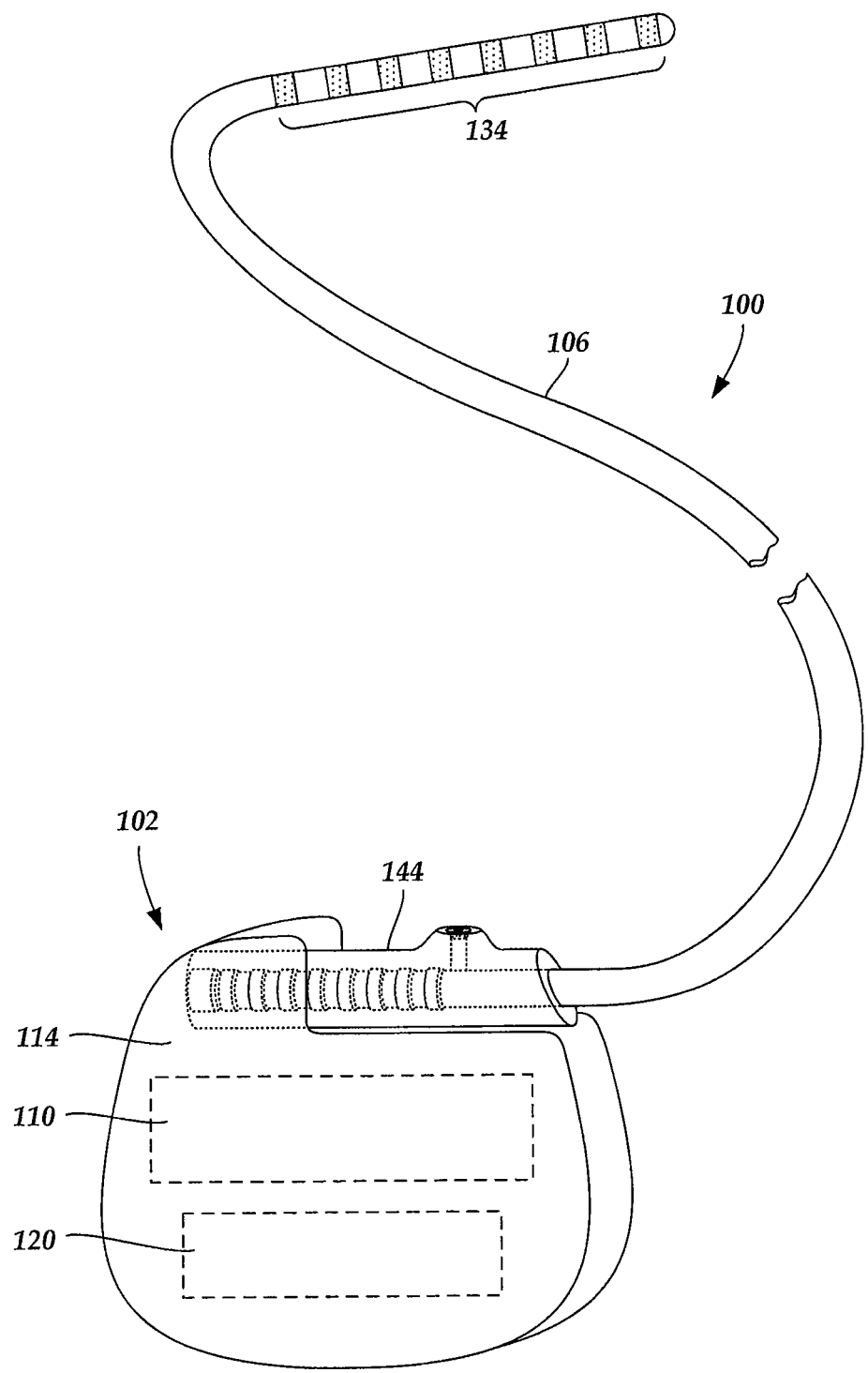
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In at least some embodiments, it may be advantageous to for the lead to be isodiametric along the length of the lead in order to allow the lead to pass through an insertion needle during implantation in order to minimize the invasiveness of an implantation procedure. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes disposed at the distal end of the lead are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
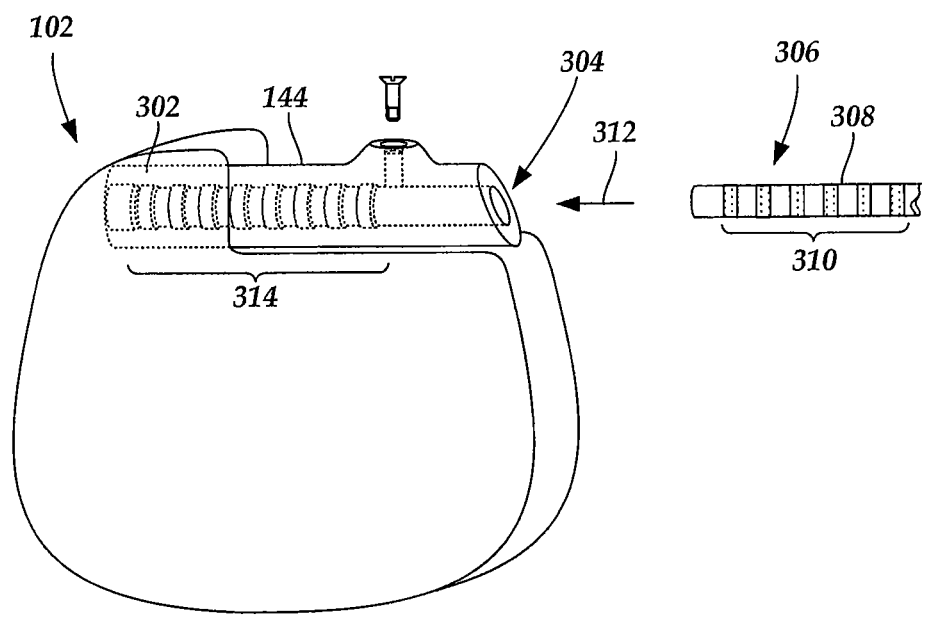
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532, 844, which are incorporated by reference.

Figure 3B:
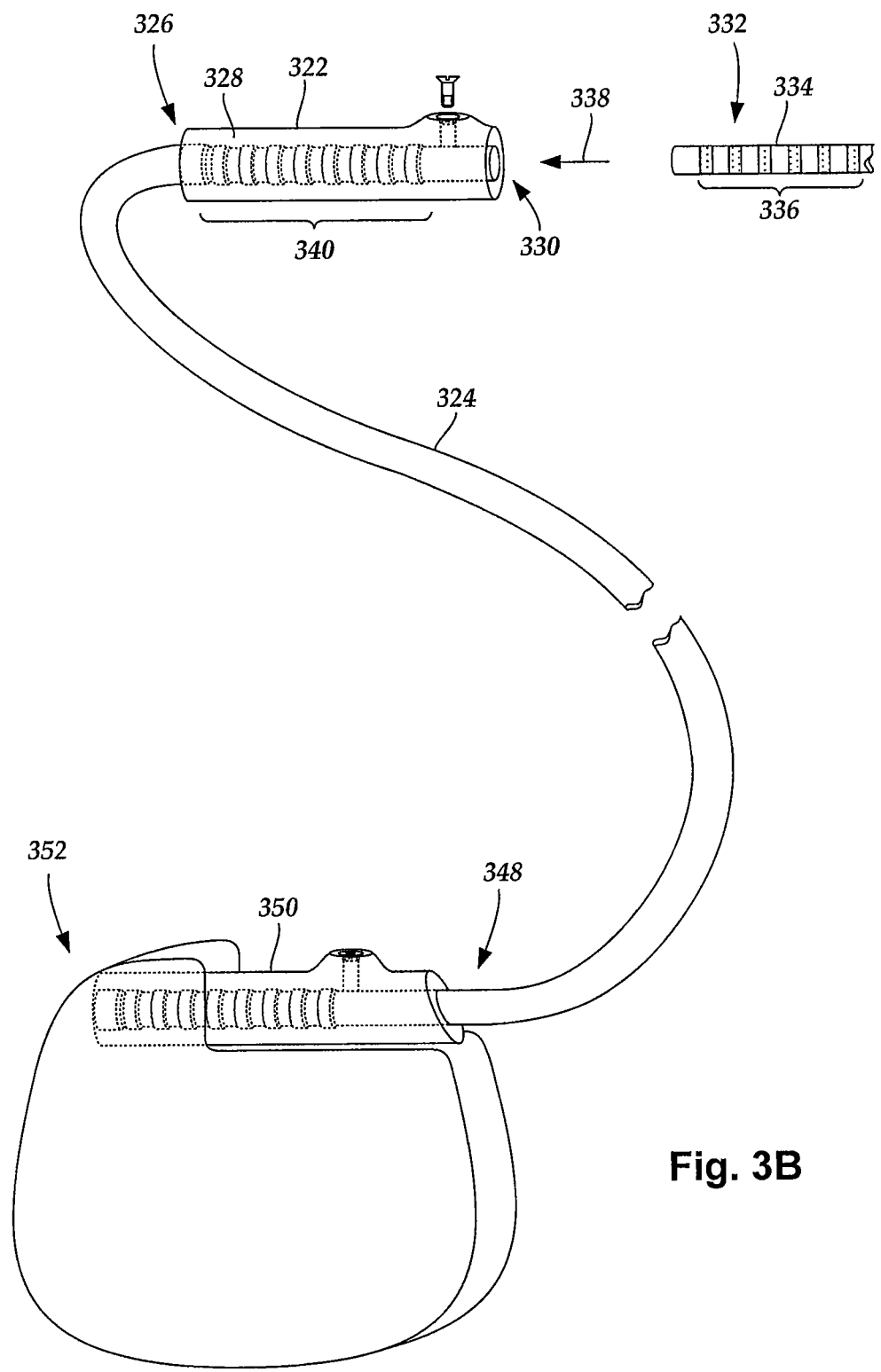
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

Sometimes, implantation of a lead into a patient is facilitated by using a stylet. A stylet may be disposed in one or more lumens defined in a lead to provide increased rigidity to the lead, as well as to provide a proximally-positioned handle, or "cap," for maneuvering the stylet and lead within a patient. Implantation of a lead may further be facilitated by using an insertion needle, such as an epidural needle. For example, an insertion needle may be percutaneously inserted into a patient. Once the insertion needle is positioned, a lead-inserted stylet may be used to maneuver the distal end of the lead within the insertion needle or within patient tissue.

Insertion of a stylet into one or more lumens of a lead, or maneuvering the stylet within the lead, may potentially damage a lead. For example, a distal end of a stylet may penetrate an outer lead covering, resulting in a hole in the outer lead covering. In at least some embodiments, force may be applied to a cap or a proximal portion of a stylet while maneuvering a distal portion of the stylet disposed in a lead. The amount of force needed to maneuver the distal portion of the stylet disposed in the lead may vary depending on the anatomy of a patient. For example, maneuvering around narrow bends may require application of a greater amount of force than maneuvering along an expansive straightaway. Sometimes, when resistance is encountered and additional force is applied to compensate, the additional force may cause the distal portion of the stylet to damage, or even penetrate, an outer lead covering of the lead. The risk of the stylet damaging an outer lead covering may be increased when the distal end of the lead is not disposed in an insertion needle, such as when an insertion needle is not used during lead implantation, or when the distal end of the stylet extends beyond an open tip of an insertion needle.

In at least some embodiments, a stylet is described that is configured and arranged to reduce the risk of the stylet damaging or penetrating an outer lead covering. In at least some embodiments, the risk of the stylet damaging or penetrating the outer lead covering of the lead is reduced by the stylet absorbing or redirecting an amount of force in excess of a threshold amount of force. In at least some embodiments, the threshold amount of force is based, at least in part, on the amount of force needed for a stylet to damage or penetrate an outer lead cover. In at least some embodiments, the absorption or redirection of the excess force may provide a tactile signal to an applier of the force ("a user") that excessive force is being used.

Figure 4:
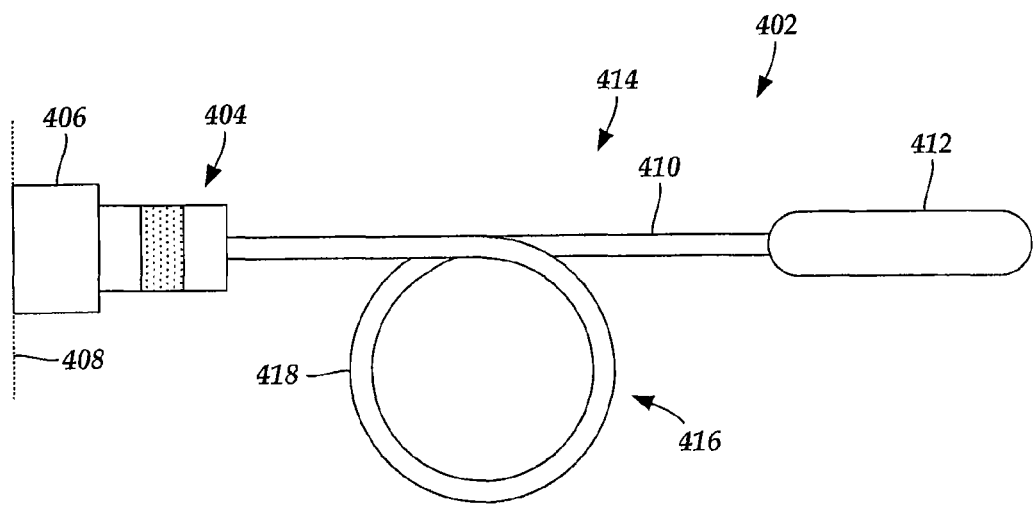
FIG. 4 is a schematic side view of one embodiment of a stylet inserted into a proximal end of a lead, the stylet including a loop in a body of the stylet, according to the invention.

FIG. 4 is a schematic side view of one embodiment of a distal portion of a stylet 402 inserted into a proximal end of a lead 404. In at least some embodiments, the lead 404 may be disposed in an insertion needle 406. In at least some embodiments, the insertion needle 406 may be inserted in a patient, represented in FIG. 4 and in subsequent figures as a dotted line 408. The stylet 404 includes an elongated body 410 and a cap 412 coupled to a proximal portion 414 of the elongated body 410. The stylet 402 may be formed from any biocompatible material of adequate stiffness suitable for implantation into a patient including, for example, wire, stainless steel, titanium, nitinol, and the like or combinations thereof.

In at least some embodiments, application of an amount of force to the stylet 402 in excess of a force threshold, particularly during insertion or maneuvering of the stylet, results in a portion of the force being absorbed, or redirected to a portion of the stylet 402. In at least some embodiments, application of excessive force may result in damage or penetration of an outer lead covering of the lead 404 by a distal end of the stylet 402. It will be recognized that what constitutes excessive force may depend on many different factors, such as lead arrangement, lead materials, stylet size, stylet materials, and the like or combinations thereof.

In at least some embodiments, a protective feature 416 is included in the elongated body 410 of the stylet 402 to absorb or redirect an amount of force in excess of a force threshold when some amount of resistance is encountered, such as during insertion or maneuvering of the stylet 402. In at least some embodiments, the protective feature 416 is configured and arranged to prevent or reduce the possibility of damaging or penetrating an outer lead covering. In FIG. 4, the protective feature 416 is shown as a loop 418 in an elongated body 410 of the stylet 404. In some embodiments, the loop 418 has a circular shape. In other embodiments, the loop 418 has a non-circular shape, such as an oval-shape, triangular-shape, rectangular-shape, or the like. In at least some embodiments, the loop 418 is configured and arranged so that when resistance is encountered (i.e., friction from the walls of the lumen) while force is applied to the cap 412 or to the elongated body 410 proximal to the loop 418 in certain directions, such as in one or more distal directions (i.e., while maneuvering the distal portion of the elongated body 410 disposed in the lead 404), application of the force above a force threshold is absorbed or redirected by the loop 418, thereby causing the diameter of the loop 418 to expand. In at least some embodiments, an expansion of the loop 418 may be used as a tactile signal to the user that an applied force exceeds a force threshold. In at least some embodiments, the protective feature 416 may include multiple loops, either spaced apart individually or continuous in a spiral or helix.

Figure 5:
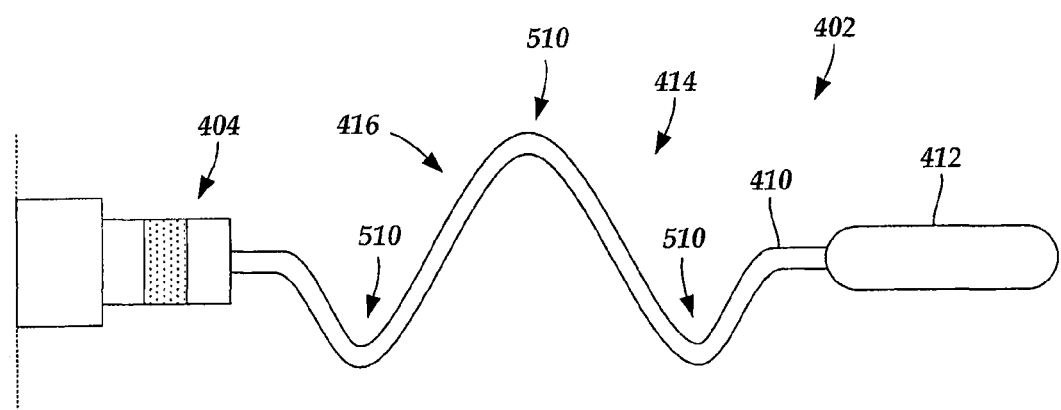
FIG. 5 is a schematic side view of a second embodiment of a stylet inserted into a proximal end of a lead, the stylet including kinks in an elongated body of the stylet, according to the invention.

In at least some embodiments, the protective feature 416 may include one or more kinks in the elongated body 410 of the stylet 402. FIG. 5 is a schematic side view of a second embodiment of the stylet 402 inserted into a proximal end of the lead 404. The proximal portion 414 of the elongated body 410 of the stylet 402 includes the protective feature 416. In FIG. 5, the protective feature 416 includes one or more kinks 502. In at least some embodiments, the one or more kinks 502 each include a twist or curl causing the elongated body 410 to double back on itself. The one or more kinks 502 may take many different regular or irregular forms including, for example, a sine-wave pattern, a triangular-wave pattern, a square-wave pattern, and the like or combinations thereof. In at least some embodiments, when more than one kink 502 is employed, each kink 502 has an approximately equal radius. In at least some embodiments, when more than one kink 502 is employed, at least two of the kinks 502 have different radii.

In at least some embodiments, the one or more kinks 502 are configured and arranged so that when resistance is encountered while force is applied to the cap 412 or to the elongated body 410 proximal to the one or more kinks 502 in certain directions, such as in one or more distal directions (i.e., while maneuvering the distal portion of the elongated body 410 disposed in the lead 404), application of the force above a force threshold is absorbed by the one or more kinks 502, causing the one or more kinks 502 to flex. In at least some embodiments, a flexing of the one or more kinks 502 may be used as a tactile signal to a user that an applied force exceeds a force threshold. In at least some embodiments, the protective feature 416 may include a combination of one or more loops 418 and one or more kinks 502. It will be understood that the protective feature 416 may also include many other different shapes, both regular and irregular.

Figure 6:
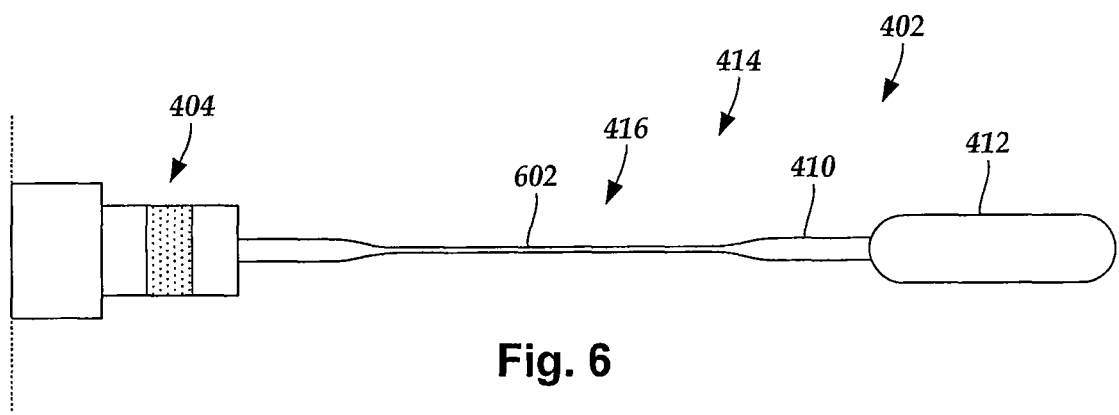
FIG. 6 is a schematic side view of a third embodiment of a stylet inserted into a proximal end of a lead, the stylet including a reduced-diameter section in an elongated body of the stylet, according to the invention.

In at least some embodiments, the protective feature 416 may include one or more reduced-diameter sections disposed in the elongated body 410 of the stylet 402. FIG. 6 is a schematic side view of a third embodiment of the stylet 402 inserted into the proximal end of the lead 404. The proximal portion 414 of the elongated body 410 of the stylet 402 includes the protective feature 416. In FIG. 6, the protective feature 416 includes one or more reduced-diameter sections 602 disposed in the elongated body 410 of the stylet 402.

In at least some embodiments, the one or more reduced-diameter sections 602 are configured and arranged so that when resistance is encountered while force is applied to the cap 412 or to the elongated body 410 proximal to the one or more reduced-diameter sections 602 in certain directions, such as in one or more distal directions (i.e., while maneuvering the distal portion of the elongated body 410 disposed in the lead 404), application of the force above a force threshold causes the one or more reduced-diameter sections 602 to buckle. In at least some embodiments, a buckling of the one or more reduced-diameter sections 602 may be used as a tactile signal to a user that an applied force exceeds a force threshold.

The one or more reduced-diameter sections 602 may be many different lengths. In at least some embodiments, when more than one reduced-diameter section 602 is employed, each reduced-diameter section 602 is of approximately equal length. In at least some embodiments, when more than one reduced-diameter section 602 is employed, at least two of the reduced-diameter sections 602 have different lengths. In at least some embodiments, the reduced-diameter sections 602 have a length that is no more than fifty percent of the length of the stylet 402. In at least some embodiments, the reduced-diameter sections 602 have a length that is no more than twenty-five percent of the length of the stylet 402. In at least some embodiments, the reduced-diameter sections 602 have a length that is no more than ten percent of the length of the stylet 402. In at least some embodiments, the reduced-diameter sections 602 have a length that is no more than five percent of the length of the stylet 402. In at least some embodiments, the one or more reduced-diameter sections 602 each have a length of at least one-half inch (1.77 cm). In at least some embodiments, the one or more reduced-diameter sections 602 each have a length of no more than four inches (10.16 cm). In a preferred embodiment, the one or more reduced-diameter sections 602 each have a length approximately within a range of one inch to two inches (2.54 cm to 5.08 cm).

In at least some embodiments, the reduced-diameter sections 602 have a diameter that is no more than eighty percent of the diameter of the stylet 402. In at least some embodiments, the reduced-diameter sections 602 have a diameter that is no more than sixty percent of the diameter of the stylet 402. In at least some embodiments, the reduced-diameter sections 602 have a diameter that is no more than forty percent of the diameter of the stylet 402. In at least some embodiments, the reduced-diameter sections 602 have a diameter that is no more than twenty percent of the diameter of the stylet 402. In at least some embodiments, the stylet 402 has a diameter of approximately 0.012 inches to 0.014 inches (0.030 cm to 0.036 cm). In at least some embodiments, when the stylet 402 has a diameter of approximately 0.012 inches to 0.014 inches (0.030 cm to 0.036 cm), the diameters of the one or more reduced-diameter sections 602 are less than approximately 0.012 inches (0.030 cm). In at least some embodiments, when the stylet 402 has a diameter of approximately 0.012 inches to 0.014 inches (0.030 cm to 0.036 cm), the diameters of the one or more reduced-diameter sections 602 are greater than approximately 0.002 inches (0.005 cm). In a preferred embodiment, when the stylet 402 has a diameter of approximately 0.012 inches to 0.014 inches (0.030 cm to 0.036 cm), the diameters of the one or more reduced-diameter sections 602 are each approximately within a range of approximately 0.006 to 0.008 inches (0.015 cm to 0.020 cm).

In at least some embodiments, the protective feature 416 may include a combination of one or more loops 418, one or more kinks 502, and one or more reduced-diameter sections 602. It will be understood that the protective feature 416 may also include many other different shapes, both regular and irregular, along with one or more reduced-diameter sections 602.

Figure 7A:
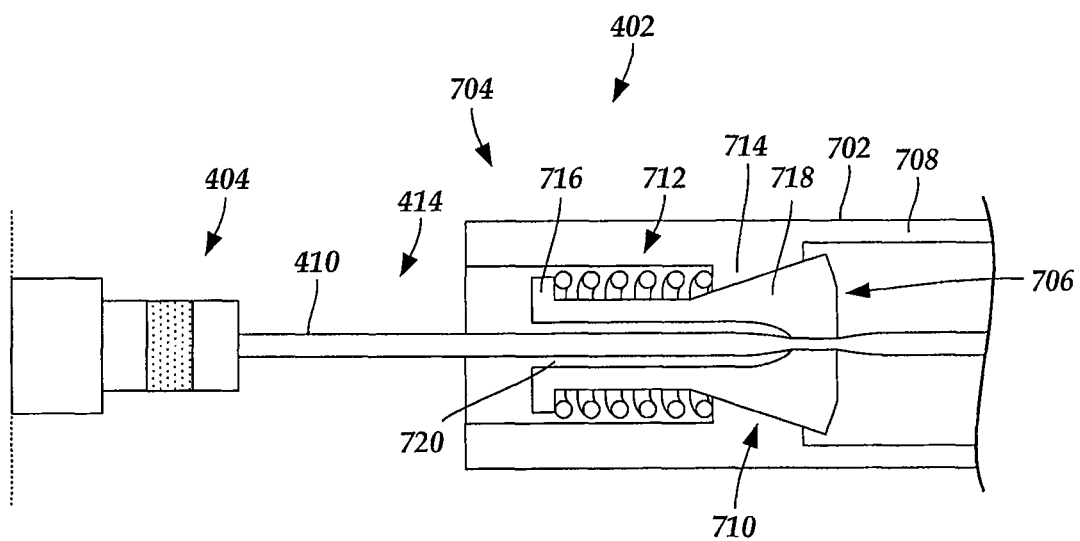
FIG. 7A is a schematic longitudinal cross-sectional view of a fourth embodiment of a stylet inserted into a proximal end of a lead, the stylet including a section of a proximal portion of an elongated body being squeezed by a clutch mechanism disposed in a cap, according to the invention.

In at least some embodiments, a protective feature may be at least partially disposed in the cap 412. FIG. 7A is a schematic longitudinal cross-sectional view of a fourth embodiment of the stylet 402 inserted into a proximal end of the lead 404. The stylet 402 includes a cap 702 with a distal end 704. The cap 702 includes a clutch mechanism 706 disposed in the cap 702 that may operate as a protective feature. The cap 702 includes an outer housing 708, an inner housing 710 disposed in the outer housing 708, and a spring 712 disposed over a portion of the inner housing 710. The outer housing 708 includes an outer flange 714. The inner housing 710 includes an interference flange 716 and one or more clamping members 718. In at least some embodiments, the one or more clamping members 718 include a split collet. The inner housing 710 also defines a lumen 720. The clutch mechanism 706 includes at least the inner housing 710, the spring 712, and the outer flange 714 of the outer housing 708. Note that only the proximal end 704 of the outer housing 708 is shown in FIG. 7A for clarity of illustration.

In at least some embodiments, the proximal portion 414 of the elongated body 410 of the stylet 402 is configured and arranged for insertion into the distal end 704 of the cap 702. In at least some embodiments, the proximal portion 414 of the elongated body 410 of the stylet extends through the lumen 720 defined in the inner housing 710. In at least some embodiments, at least one section of the proximal portion 414 of the elongated body 410 of the stylet 402 provides resistance (i.e., squeezing, an interference fit, and the like) by the one or more clamping members 718 by some amount of force. In at least some embodiments, the resistive force with which the one or more clamping members 718 provides against at least one section of the proximal portion 414 of the elongated body 410 is at least partially determined by a spring constant of the spring 712. In at least some embodiments, the spring 712 is maintained in a compressed state between the interference flange 716 and the outer flange 714. The decompression force from the spring 712 pushes against the outer flange 714 which, in turn, pushes against the one or more clamping members 718. Accordingly, in at least some embodiments the force with which the spring 712 pushes against the outer flange 714 is proportional to the resistive force with which the cap 702 applies against the proximal portion 414 of the elongated body 410.

In at least some embodiments, the spring 712 may be configured and arranged so that the elongated body 410 slides along the cap 702 when resistance is encountered while applying a force that exceeds a force threshold. In at least some embodiments, the wire penetrates an outer lead covering of a lead when a minimum force of at least 0.50 pounds is applied to the stylet. Thus, as an example, when it is desired to disallow application of a force to the cap 702 exceeding a force threshold of 0.50 pounds, the clutch mechanism 706 can be adjusted so that an applied force of at least 0.30 pounds, or at least 0.40 pounds, or at least 0.45 pounds exceeds the resistive force with which the clamping mechanisms 718 provides against the elongated body 410, thereby causing the elongated body 410 to slide along the cap 702.

In at least some embodiments, the cap 702 is configured and arranged so that when resistance is encountered while force is applied to the cap 702 in certain directions, such as in one or more distal directions (i.e., while maneuvering the distal portion of the elongated body 410 disposed in the lead 404), application of the force above a force threshold exceeds the resistive force with which the one or more clamping members 718 provide against the proximal portion 414 of the elongated body 410 and causes the stylet 402 to slide against the cap 702. In at least some embodiments, the sliding of the stylet 402 along the cap 702 may be used as a tactile signal to a user that an applied force exceeds a force threshold.

Sometimes it is desirable to maintain a given orientation of the elongated body 410 of the lead 404 as the lead 404 is maneuvered (via the stylet 402) in a patient (for example, when asymmetrically-placed electrodes on a distal end of the lead need to be positioned in a certain orientation). Maintaining a given orientation during lead implantation may be difficult when applying force in one or more directions while maneuvering the lead 404 (via the stylet 402) in the patient. Maintaining a given orientation may be made more difficult when the application of force to the cap 702 causes the elongated body 410 to rotate relative to the cap 702. Accordingly, in at least some embodiments the proximal portion 414 of the elongated body 410 of the stylet 402 includes one or more sections with non-cylindrical cross-sectional shapes. In at least some embodiments, the one or more non-cylindrical sections may be positioned so that resistive force is applied by the one or more clamping members 718 to the elongated body 410 of the stylet 402 at the one or more non-cylindrical sections. In at least some embodiments, when resistive force is applied by the one or more clamping members 718 to the elongated body 410 of the stylet 402 at the one or more non-cylindrical sections, the elongated body 410 is prevented from rotating relative to the cap 702.

Figure 7B:
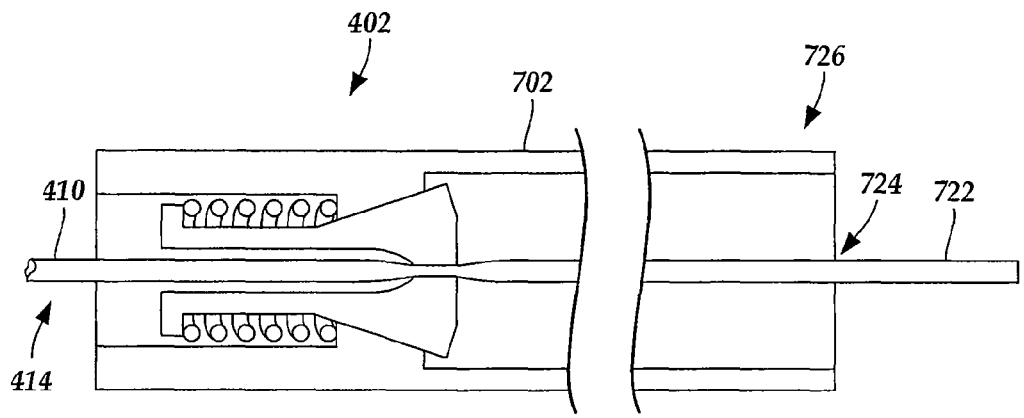
FIG. 7B is a schematic longitudinal cross-sectional view of the fourth embodiment of the stylet shown in FIG. 7A, the stylet including a proximal tip of an elongated body extending from a port defined in a proximal end of a cap, according to the invention.

When force above a force threshold is applied to the cap 702 while encountering resistance, and the elongated body 410 slides along the cap 702, the distance that the elongated body 410 slides may exceed a distance between the one or more clamping members 718 and a proximal end of the cap 702. In at least some embodiments, the cap 702 includes a proximal end that is at least partially open. In at least some embodiments, the cap 702 includes a port defined in the proximal end of the cap 702 through which a proximal tip of the elongated body 410 may extend. FIG. 7B is a schematic longitudinal cross-sectional view of a proximal portion of the fourth embodiment of the stylet 402 that includes resistive force being applied to the proximal portion 414 of the elongated body 410 by the cap 702. A proximal tip 722 of the elongated body 410 extends through a port 724 defined in a proximal end 726 of the cap 702.

Figure 7C:
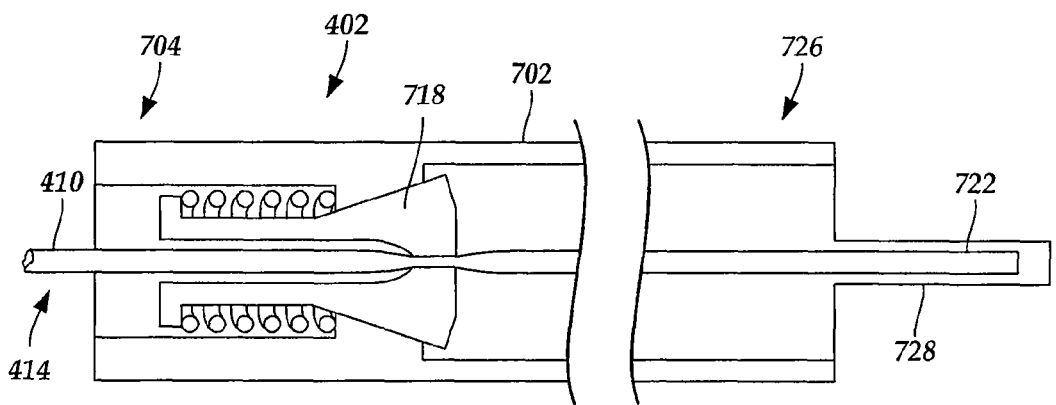
FIG. 7C is a schematic longitudinal cross-sectional view of the fourth embodiment of the stylet shown in FIG. 7A, the stylet including a proximal tip of an elongated body extending into an extension tube disposed in a proximal end of a cap, according to the invention.

The proximal tip 722 of the elongated body 410 projecting through the port 724 may catch a user unaware and consequently cause an injury, such as impalement, or some other type of damage. Accordingly, in at least some embodiments, the proximal tip 722 may include one or more curls or bends or a blunt tip to reduce the risk of causing injury or damage. In some embodiments, an expansion tube is disposed at the proximal end 726 of the cap 702 to at least partially enclose the proximal tip 722 of the elongated body 410 when the proximal tip 722 extends beyond the proximal end 726 of the cap 702 to reduce the potential risk of injury or damage. FIG. 7C is a schematic longitudinal cross-sectional view of the fourth embodiment of the stylet 402 that includes a resistive force being applied to the proximal portion 414 of the elongated body 410 by the cap 702. The cap 702 includes an extension tube 728 extending in a proximal direction from the proximal end 726 of the cap 702. The extension tube 728 is configured and arranged to at least partially enclose the proximal tip 722 of the elongated body 410 when the proximal tip 722 extends beyond the proximal end 726 of the cap 702. In a preferred embodiment, at least a portion of the lateral circumference of the extension tube 728 is at least as great as a lateral circumference of the elongated body 410. In at least some embodiments, the distance from the one or more clamping members 718 to a proximal-most portion of the extension tube 728 is at least as great as the distance between the distal end 704 of the cap 702 and a proximal end of the lead (404 in FIG. 4). In at least some embodiments, a proximal-most portion of the extension tube 728 is open so that the proximal tip 722 of the elongated body 410 may extend beyond the extension tube 728.

Figure 7D:
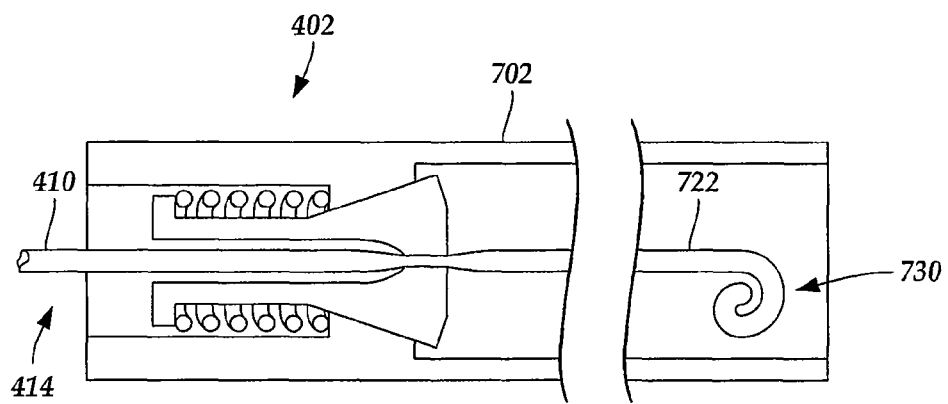
FIG. 7D is a schematic longitudinal cross-sectional view of the fourth embodiment of the stylet shown in FIG. 7A, the stylet including a section of a proximal portion of an elongated body being squeezed by a cap, the elongated body including a curled proximal tip, according to the invention.

In at least some embodiments, the proximal end 726 of the cap 702 includes neither the port 724 nor the extension tube 728. In at least some embodiments, the distance from the one or more clamping members 718 to the proximal end 726 of the cap 702 is at least as great as the distance between the distal end 704 of the cap 702 and a proximal end of the lead (404 in FIG. 4). In at least some embodiments, the proximal tip 722 of the elongated body 410 includes a curl. FIG. 7D is a schematic longitudinal cross-sectional view of the fourth embodiment of the stylet 402 that includes resistive force being applied to the proximal portion 414 of the elongated body 410 by the cap 702. The proximal tip 722 of the elongated body 410 of the stylet 402 includes a curl 730. In at least some embodiments, when the stylet 402 slides along the cap 702, the curl 730 prevents the proximal tip 722 of the elongated body 410 of the stylet 402 from reaching the proximal end 726 of the cap 702. In at least some embodiments, when the stylet 402 slides along the cap 702, the curl 730 causes the proximal tip 722 of the elongated body 410 to bend against the proximal end 726 of the cap 702.

Figure 8:
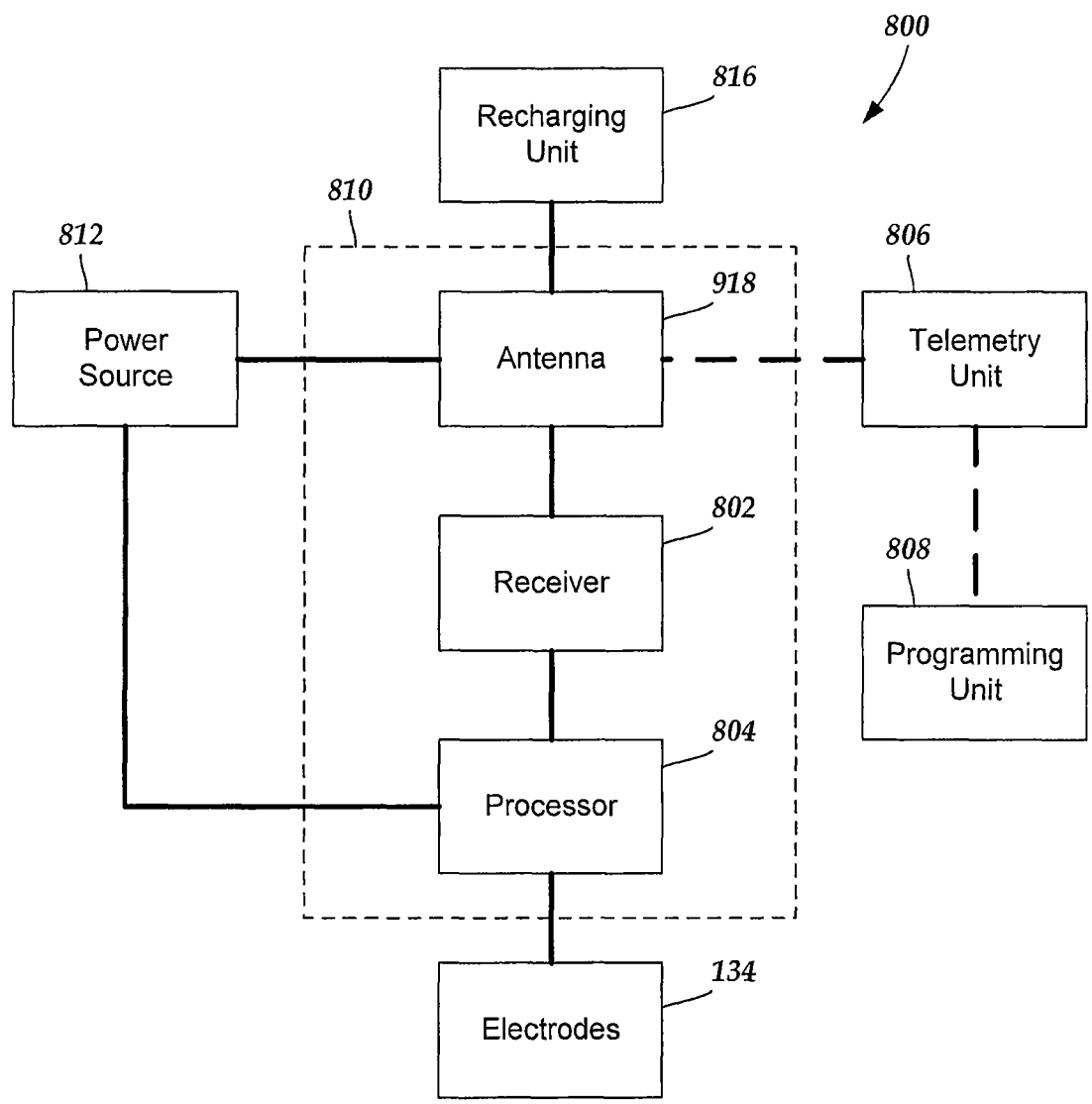
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stylet comprising
an elongated body with a distal portion, a proximal portion, and a proximal tip; and
a cap having a proximal end and a distal end, the cap comprising
an inner housing defining a central lumen, the central lumen configured and arranged to receive the proximal portion of the elongated body, the inner housing comprising an interference flange and at least one clamping member, the at least one clamping member configured and arranged for providing resistive force against the elongated body,
an outer housing comprising an outer flange configured and arranged to press against at least one of the clamping members, and
a compressed spring positioned between the interference flange and the outer flange, an initial compression value of the compressed spring at least partially determining the amount of force with which the outer flange presses against at least one of the clamping members.

2. The stylet of claim 1, further including a port defined in the proximal end of the outer housing, the port configured and arranged to receive the proximal tip of the elongated member.

3. The stylet of claim 1, further including an extension tube disposed in the proximal end of the outer housing, the extension tube configured and arranged to receive the proximal tip of the elongated body.

4. The stylet of claim 1, wherein the proximal tip of the elongated body is curled.

5. The stylet of claim 1, wherein the proximal portion of the elongated body comprises at least one section with a non-circular cross-sectional shape.

6. A lead assembly comprising
a lead with a distal end and a proximal end, the lead comprising
a plurality of electrodes disposed at the distal end,
a plurality of terminals disposed at the proximal end,
at least one lumen defined in the lead, the at least one lumen extending from the distal end to the proximal end, and
a plurality of conductive wires electrically coupling the plurality of electrodes electrically to the plurality of terminals; and
the stylet of claim 1.

7. An electrical stimulating system comprising:
a lead with a distal end and a proximal end, the lead comprising
a plurality of electrodes disposed along the distal end,
a plurality of terminals disposed along the proximal end,
at least one lumen defined in the lead, the at least one lumen extending from the distal end to the proximal end, and
a plurality of conductive wires electrically coupling the plurality of electrodes electrically to the plurality of terminals;
the stylet of claim 1;
a control module configured and arranged to electrically couple to the proximal end of the lead of the lead assembly, the control module comprising
a housing, and
an electronic subassembly disposed in the housing; and
a connector for receiving the lead, the connector having a proximal end, a distal end, and a longitudinal length, the connector comprising
a connector housing defining a port at the distal end of the connector, the port configured and arranged for receiving the proximal end of the lead, and
a plurality of connector contacts disposed in the connector housing, the connector contacts configured and arranged to couple to at least one of the plurality of terminals disposed on the proximal end of the lead.

8. A method for stimulating patient tissue, the method comprising:
providing the stylet of claim 1;
disposing a distal portion of the stylet into one or more lumens defined in a lead;
inserting the lead and stylet into a patient, the lead comprising a plurality of electrodes disposed on a distal end electrically coupled to a plurality of terminals disposed on a proximal end by a plurality of conductive wires electrically coupling at least one terminal to at least one electrode;
guiding the lead and the stylet to a desired location in the patient using the cap disposed on the proximal portion of the stylet,
using a protective feature of the stylet to absorb or redirect an amount of force applied to the cap above a preselected force threshold while guiding the lead and stylet;
removing the stylet from the lead;
disposing the proximal end of the lead into a connector, the connector defining a port for receiving the proximal end of the lead, the port comprising a plurality of connective contacts that electrically couple to at least one of the plurality of terminals, the connector electrically coupled to a control module; and
providing electrical signals from the control module to electrically stimulate patient tissue using at least one of the electrodes on the lead.

9. The method of claim 8, wherein using a protective feature of the stylet comprises using a protective feature disposed on the elongated body.

10. The method of claim 8, wherein using a protective feature of the stylet comprises using the compressed spring, positioned between the interference flange and the outer flange of the cap.

11. The method of claim 8, wherein using a protective feature of the stylet comprises receiving a tactile signal from the protective feature when the amount of force applied to the cap exceeds a threshold amount of force.

12. The method of claim 8, wherein the preselected force threshold is no greater than a minimum amount of force needed for the distal portion of the elongated body of the stylet to damage or penetrate the outer lead covering of the lead.

* * * * *